United States Patent
Park et al.

(10) Patent No.: US 12,251,425 B2
(45) Date of Patent: *Mar. 18, 2025

(54) SUSTAINED-RELEASE LIPID PREFORMULATION AND PHARMACEUTICAL COMPOSITION FOR SUSTAINED-RELEASE INJECTION IN FORM OF LIPID SOLUTION CONTAINING SAME

(71) Applicant: IMDPHARM INC., Suwon-si (KR)

(72) Inventors: Young-Joon Park, Seoul (KR); Sang-Won Jeon, Suwon-si (KR); Sook Choi, Seoul (KR)

(73) Assignee: IMDPHARM INC., Suwon-si (KR)

( * ) Notice: Subject to any disclaimer, the term of this patent is extended or adjusted under 35 U.S.C. 154(b) by 635 days.

This patent is subject to a terminal disclaimer.

(21) Appl. No.: 17/310,689

(22) PCT Filed: Feb. 17, 2020

(86) PCT No.: PCT/KR2020/002182
§ 371 (c)(1),
(2) Date: Aug. 18, 2021

(87) PCT Pub. No.: WO2020/171491
PCT Pub. Date: Aug. 27, 2020

(65) Prior Publication Data
US 2022/0125888 A1    Apr. 28, 2022

(30) Foreign Application Priority Data

Feb. 18, 2019  (KR) .................... 10-2019-0018619

(51) Int. Cl.
| | | |
|---|---|---|
| *A61K 9/00* | (2006.01) | |
| *A61K 31/445* | (2006.01) | |
| *A61K 31/519* | (2006.01) | |
| *A61K 31/522* | (2006.01) | |
| *A61K 38/09* | (2006.01) | |
| *A61K 38/26* | (2006.01) | |
| *A61K 38/31* | (2006.01) | |
| *A61K 47/12* | (2006.01) | |
| *A61K 47/14* | (2017.01) | |
| *A61K 47/22* | (2006.01) | |
| *A61K 47/24* | (2006.01) | |

(52) U.S. Cl.
CPC ............ *A61K 38/31* (2013.01); *A61K 9/0019* (2013.01); *A61K 31/445* (2013.01); *A61K 31/519* (2013.01); *A61K 31/522* (2013.01); *A61K 38/09* (2013.01); *A61K 38/26* (2013.01); *A61K 47/12* (2013.01); *A61K 47/14* (2013.01); *A61K 47/22* (2013.01); *A61K 47/24* (2013.01)

(58) Field of Classification Search
None
See application file for complete search history.

(56) References Cited

U.S. PATENT DOCUMENTS

| | | |
|---|---|---|
| 5,993,850 A | 11/1999 | Sankaram et al. |
| 6,340,475 B2 | 1/2002 | Shell et al. |
| 9,526,787 B2 | 12/2016 | Ko et al. |
| 2001/0018070 A1 | 8/2001 | Shell et al. |
| 2002/0102301 A1 | 8/2002 | Schwarz |
| 2003/0072798 A1 | 4/2003 | Schwarz |
| 2005/0037073 A1 | 2/2005 | Schwarz |
| 2014/0206616 A1 | 7/2014 | Ko et al. |
| 2015/0265535 A1* | 9/2015 | Yu .................... A61K 47/24 424/85.4 |

FOREIGN PATENT DOCUMENTS

| | | | | |
|---|---|---|---|---|
| CN | 106491519 A | * | 3/2017 | ............ A61K 31/167 |
| WO | WO-9847487 A1 | * | 10/1998 | ............ A61K 9/1274 |
| WO | 2005/117830 A1 | | 12/2005 | |

OTHER PUBLICATIONS

Machine Translation of Chen CN-106491519-A (abstract only) WIPO [online] .2017 [retrieved on Feb. 9, 2024]. Retrieved from the Internet: <https://patentscope.wipo.int/search/en/detail.jsf?docId=CN194489261&_cid=P12-LSF682-78425-1> (Year: 2017).*
Comelles, F., Sánchez-Leal, J. and González, J.J. (2005), Influence of fatty acid structure on liquid crystal formation in systems with anionic surfactant, diethyleneglycol ethylether and water. Eur. J. Lipid Sci. Technol., 107: 291-296. https://doi.org/10.1002/ejlt.200401116 (Year: 2005).*
Schaschke et al, High Pressure Research 27 (1), pp. 33-37. (Year: 2007).*
Span(R)80 PubChem entry [online]. Pubchem (2017) [retrieved on Aug. 28, 2024]. Retrieved from the internet: <https://pubchem.ncbi.nlm.nih.gov/substance/329769385>. (Year: 2017).*

(Continued)

*Primary Examiner* — Katherine Peebles
*Assistant Examiner* — Afua Bamfoaa Boateng
(74) *Attorney, Agent, or Firm* — Vorys, Sater, Seymour and Pease LLP; Mih Suhn Koh

(57) ABSTRACT

Provided is a sustained-release lipid pre-concentrate in the form of a lipid solution, including an unsaturated fatty acid having 14 to 20 carbon atoms (C14~C20); a phospholipid; and α-tocopherol acetate, wherein the sustained-release lipid pre-concentrate is free of diacyl glycerol and sorbitan unsaturated fatty acid ester; and forms a liquid crystal in an aqueous medium. Further provided is a sustained-release injectable pharmaceutical composition in the form of a lipid solution, including the pre-concentrate and a pharmacologically active substance, wherein the sustained-release injectable pharmaceutical composition is free of diacyl glycerol and sorbitan unsaturated fatty acid ester.

19 Claims, 8 Drawing Sheets

(56) References Cited

OTHER PUBLICATIONS

Schashcke: oleic acid viscosity (Year: 2007).*
Sorbitan monooleate viscosity from PubChem (Year: 2017).*

* cited by examiner

SUSTAINED-RELEASE LIPID PREFORMULATION AND PHARMACEUTICAL COMPOSITION FOR SUSTAINED-RELEASE INJECTION IN FORM OF LIPID SOLUTION CONTAINING SAME

TECHNICAL FIELD

The present invention relates to a sustained-release lipid pre-concentrate and a sustained-release injectable pharmaceutical composition in the form of a lipid solution comprising the same. More specifically, the present invention relates to a sustained-release lipid pre-concentrate, comprising a combination of an unsaturated fatty acid having 14 to 20 carbon atoms ($C_{14}$~$C_{20}$); a phospholipid; and α-tocopherol acetate and a sustained-release injectable pharmaceutical composition in the form of a lipid solution comprising the same.

BACKGROUND ART

Many pharmacologically active substances including macromolecular biopharmaceuticals such as peptides, proteins, nucleic acids, and viruses, as well as small-molecular synthetic compounds, especially those with short residence time in the body should be administered repeatedly within a short period of time in order to maintain the therapeutically effective concentration thereof. Such repeated administration may lead to a decrease in patient compliance, an increase in maximum blood concentration due to repeated administration and an increase in side effects thereby, and inappropriate therapeutic effects. There have been studied various methods which are applicable to oral and parenteral dosage forms for sustained release of pharmacologically active substances, in order to improve these problems. For example, there have been suggested oral formulations such as sustained-release tablets using polymers and gastric retention tablets and parenteral formulations such an extended release preparation through the skin (e.g., a transdermal patch) and an injectable preparation (e.g., subcutaneous implantation tablets, liposomes, and microspheres).

For injectable formulations for sustained release of drug, there have been mainly studied the formulations that can be administered intramuscularly or subcutaneously. Injectable formulations for sustained release of drug continuously release a physiologically active substance through single administration for several days to several weeks or months, thereby being able to maintain a therapeutically effective concentration of a drug for a long period of time and prevent side effects due to repeated administration. Most of the injectable formulations for sustained release of drug, from which the release of drug lasts for several days or more, are a formulation designed to form a drug-depot in the body and gradually release the drug into the systemic circulation. Representatively, there have been suggested a formulation in which a pharmacologically active substance is encapsulated into PLGA (a biodegradable polymer) microspheres. The microspheres are gradually decomposed into lactic acid and glycolic acid in the body, which results in slow release of the active ingredient. Polycyanamide, as well as PLGA, is also used as a biodegradable polymer used for the is preparation of microspheres. Sustained-release microsphere formulations made of a biodegradable polymer induce sustained release of a drug, thereby being able to prolong the drug's efficacy. However, biodegraded polymer particles may bring about inflammation at the injection site. Since it is also difficult to use a conventional sterile filtration method (which is one of the most industrially convenient methods) in the process for preparing a sterile formulation necessary for injection, there exists the disadvantage that it should be manufactured in a special manufacturing equipment, e.g., in a dosed aseptic processing system for sterilization.

As a formulation capable of circumventing the disadvantages of biodegradable polymer-based formulations, WO 2005/117830 discloses a liquid depot formulation comprising at least one neutral diacyl lipid (e.g., diacyl glycerol such as glyceryl dioleate) and/or at least one tocopherol; at least one phospholipid; and at least one biocompatible, oxygen containing, low-viscosity organic solvent. However, formulations containing neutral diacyl lipids, such as glyceryl dioleate, have a problem of low biodegradability. And, since neutral diacyl lipids are not a material derived from the body, their biocompatibility is limited and there is a high possibility of causing inflammation.

Korean Patent No. 10-1494594 discloses a sustained release lipid pre-concentrate comprising a sorbitan unsaturated fatty acid ester; a phospholipid such as phosphatidylcholine; and a liquid crystal hardener, free of an ionizable group (such as carboxyl group or amine group), having a hydrophobic moiety of 15 to 40 carbon atoms with a triacyl group or a carbon ring structure. And, Korean Patent No. 10-1586789 discloses a sustained release lipid pre-concentrate comprising a sorbitan unsaturated fatty acid ester; a phospholipid such as phosphatidylcholine; a liquid crystal hardener such as triglyceride and tocopherol acetate; and an anionic anchoring agent such as palmitic acid. However, since sorbitan monooleate has a high viscosity (about 1000 mPa·s, 25° C.), the formulation obtained by using the same also has a high viscosity, which leads to a problem of showing low injectability. And, sorbitan monooleate is not a component of the body nor a material derived from the body and thus may cause safety problems, e.g., inflammation at the site of administration.

Therefore, there is a need in the art to develop a sustained-release injectable pharmaceutical composition which is able to prevent the initial release of drug and has excellent biodegradability, biocompatibility and injectability, as an injectable formulation that provides sustained release of a drug for more than one week.

DISCLOSURE

Technical Problem

The present inventors carried out various studies to develop a sustained-release injectable pharmaceutical composition in the form of a lipid solution having excellent biodegradability, biocompatibility and injectability. As the results thereof, the present inventors have found that, when a pre-formulation (i.e., pre-concentrate) is prepared by combining an unsaturated fatty acid having 14 to 20 carbon atoms ($C_{14}$~$C_{20}$) (that is present in or derived from the body and is effectively biodegradable) with phospholipid and α-tocopherol acetate, instead of diacyl glycerol and/or sorbitan unsaturated fatty acid ester, and then is subject to formulation processes together with a pharmacologically active substance, it is possible to obtain a sustained-release injectable pharmaceutical composition in the form of a lipid solution having excellent injectability, biocompatibility and biodegradability.

Therefore, it is an object of the present invention to provide a sustained-release lipid pre-concentrate in the form of a lipid solution, comprising a combination of an unsaturated fatty acid having 14 to 20 carbon atoms ($C_{14}$~$C_{20}$); a phospholipid; and α-tocopherol acetate.

It is another object of the present invention to provide a sustained-release injectable pharmaceutical composition in the form of a lipid solution comprising a pharmacologically active substance; and the pre-concentrate.

Technical Solution

In accordance with an aspect of the present invention, there is provided a sustained-release lipid pre-concentrate in the form of a lipid solution, comprising an unsaturated fatty acid having 14 to 20 carbon atoms ($C_{14}$~$C_{20}$); a phospholipid; and α-tocopherol acetate, wherein the sustained-release lipid pre-concentrate is free of diacyl glycerol and sorbitan unsaturated fatty acid ester; and forms a liquid crystal in an aqueous medium.

In the pre-concentrate of the present invention, the unsaturated fatty acid having 14 to 20 carbon atoms ($C_{14}$~$C_{20}$), the phospholipid, and the α-tocopherol acetate may be present in an amount ranging from 30 to 70 wt %, in an amount ranging from 25 to 50 wt %, and in an amount ranging from 5 to 20 wt %, based on the total weight, respectively.

The pre-concentrate of the present invention may further comprise one or more organic solvents selected from the group consisting of ethanol, propylene glycol, N-methylpyrrolidone, and benzyl alcohol; or an aqueous solution of the organic solvent as a biocompatible solvent. The biocompatible solvent may be present in an amount ranging from 5 to 10 wt % based on the total weight thereof. In an embodiment, the pre-concentrate of the present invention may comprise 30 to 65 wt % of the unsaturated fatty acid having 14 to 20 carbon atoms ($C_{14}$~$C_{20}$); 25 to 50 wt % of the phospholipid; 5 to 20 wt % of α-tocopherol acetate; and 5 to 10 wt % of the biocompatible solvent.

The pre-concentrate of the present invention may further comprise a medium chain triglyceride. The medium chain triglyceride may be present in an amount ranging from 1 to 5 wt % based on the total weight thereof. In an another embodiment, the pre-concentrate of the present invention may comprise 30 to 65 wt % of the unsaturated fatty acid having 14 to 20 carbon atoms ($C_{14}$~$C_{20}$); 25 to 50 wt % of the phospholipid; 5 to 20 wt % of α-tocopherol acetate; and 1 to 5 wt % of the medium chain triglyceride. In still an another embodiment, the pre-concentrate of the present invention may comprise 30 to 55 wt % of the unsaturated fatty acid having 14 to 20 carbon atoms ($C_{14}$~$C_{20}$); 25 to 45 wt % of the phospholipid; 5 to 20 wt % of α-tocopherol acetate; 1 to 5 wt % of the medium chain triglyceride; and 5 to 10 wt % of the biocompatible solvent.

In accordance with another aspect of the present invention, there is provided a sustained-release injectable pharmaceutical composition in the form of a lipid solution, comprising a pharmacologically active substance; and the pre-concentrate, wherein the sustained-release injectable pharmaceutical composition is free of diacyl glycerol and sorbitan unsaturated fatty acid ester.

In the pharmaceutical composition of the present invention, the pharmacologically active substance may have a solubility of 0.1 mg/ml or more in the pre-concentrate, for example leuprolide or a pharmaceutically acceptable salt thereof; goserelin or a pharmaceutically acceptable salt thereof; entecavir or a pharmaceutically acceptable salt thereof; a somatostatin analogue or a pharmaceutically acceptable salt thereof; a glucagon-like peptide-1 (GLP-1) analogue or a pharmaceutically acceptable salt thereof; dutasteride or a pharmaceutically acceptable salt thereof; donepezil or a pharmaceutically acceptable salt thereof; aripiprazole or a pharmaceutically acceptable salt thereof; paliperidone or a pharmaceutically acceptable salt thereof; or risperidone or a pharmaceutically acceptable salt thereof.

In an embodiment, the pharmaceutical composition of the present invention may comprise 0.1 to 10 wt % of the pharmacologically active substance; 30 to 60 wt % of the unsaturated fatty acid having 14 to 20 carbon atoms ($C_{14}$~$C_{20}$); 25 to 50 wt % of the phospholipid; and 5 to 20 wt % of α-tocopherol acetate. In another embodiment, the pharmaceutical composition of the present invention may comprise 0.1 to 10 wt % of the pharmacologically active substance; 30 to 60 wt % of the unsaturated fatty acid having 14 to 20 carbon atoms ($C_{14}$~$C_{20}$); 25 to 45 wt % of the phospholipid; 5 to 20 wt % of α-tocopherol acetate; and 5 to 10 wt % of the biocompatible solvent. In still another embodiment, the pharmaceutical composition of the present invention may comprise 0.1 to 10 wt % of the pharmacologically active substance; 30 to 55 wt % of the unsaturated fatty acid having 14 to 20 carbon atoms ($C_{14}$~$C_{20}$); 25 to 45 wt % of the phospholipid; 5 to to 20 wt % of α-tocopherol acetate; 1 to 5 wt % of the medium chain triglyceride; and 5 to 10 wt % of the biocompatible solvent.

Advantageous Effects

The sustained-release lipid pre-concentrate in the form of a lipid solution according to the present invention; and the sustained-release injectable pharmaceutical composition in the form of a lipid solution comprising the same have a low viscosity, and thus exhibit superior injectability, in comparison with conventional pre-concentrates and sustained-release pharmaceutical compositions comprising the same. Especially, the sustained-release lipid pre-concentrate in the form of a lipid solution according to the present invention; and the sustained-release injectable pharmaceutical composition in the form of a lipid solution comprising the same comprise an unsaturated fatty acid having 14 to 20 carbon atoms ($C_{14}$~$C_{20}$) that is present in or derived from the body and is effectively biodegradable, instead of diacyl glycerol and sorbitan unsaturated fatty acid ester, and thus exhibit excellent biocompatibility and biodegradability, thereby being able to fundamentally avoid the possibility of inflammation at the site of administration which is one of the disadvantages of conventional sustained-release injectable formulations. Therefore, the present invention can provide a pharmaceutical composition in the form of a sustained release injectable formulation having excellent safety, which is capable of providing extended release for at least 7 days. In addition, the sustained-release lipid pre-concentrate in the form of a lipid solution according to the present invention; and the sustained-release injectable pharmaceutical composition in the form of a lipid solution comprising the same can be easily prepared through performing various sterile processes, including sterile filtration and the like.

BEST MODE

Figure 1:
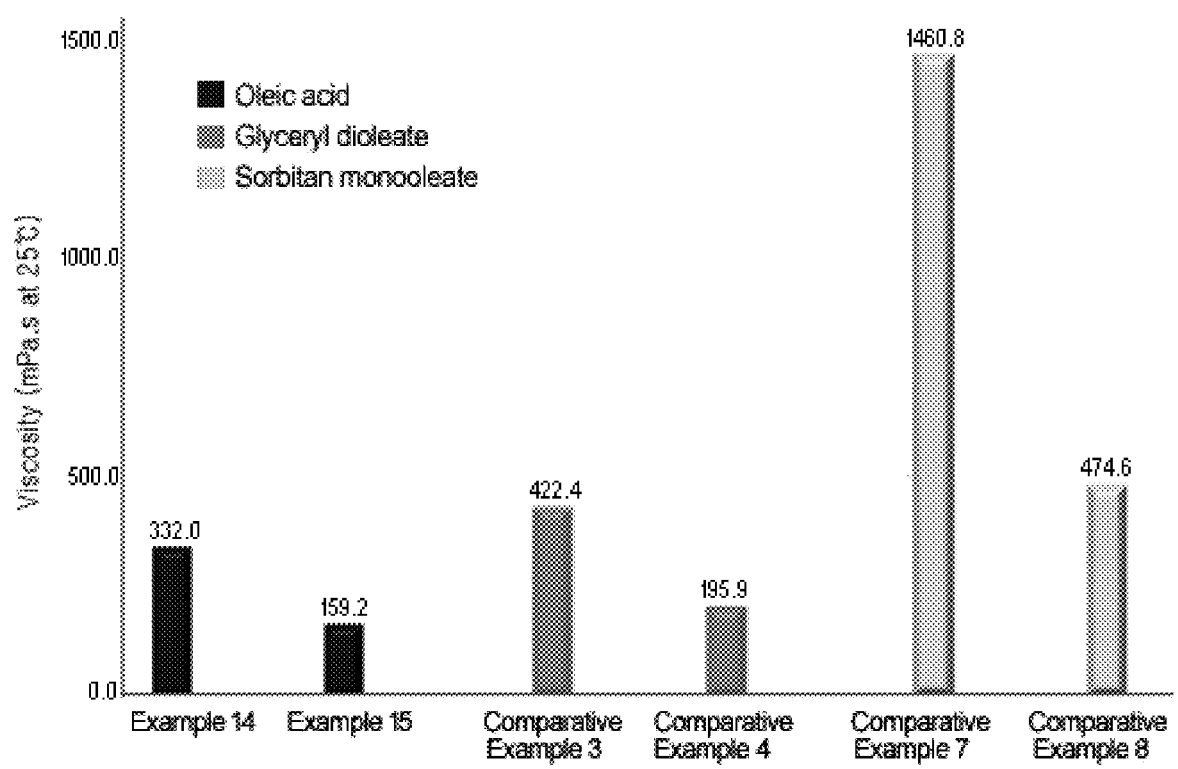
FIG. 1 shows the results obtained by measuring and comparing the viscosities of to the pre-concentrates prepared in Examples 14, 15, and Comparative Examples 3, 4, 7, and 8.

The present invention provides a sustained-release lipid pre-concentrate in the form of a lipid solution, comprising an unsaturated fatty acid having 14 to 20 carbon atoms ($C_{14}$~$C_{20}$); a phospholipid; and α-tocopherol acetate, wherein the sustained-release lipid pre-concentrate is free of diacyl glycerol and sorbitan unsaturated fatty acid ester; and forms a liquid crystal in an aqueous medium.

As used herein, the term "pre-concentrate" refers to a formulation having the form of a lipid solution, which forms a porous liquid crystal matrix having a large amount of pores of 100 nm or less, preferably 1 to 30 nm, therein, when exposed to an excess of aqueous medium (including water, biological fluid, etc.).

In the pre-concentrate of the present invention, the unsaturated fatty acid having 14 to 20 carbon atoms ($C_{14}$~$C_{20}$), which is one of the components present in the human body, plays a role in forming a porous liquid crystal matrix having a large amount of pores in nanometer units (100 nm or less, preferably 1 to 30 nm) in an aqueous medium, together with a phospholipids. Saturated fatty acids have a low ability to form a liquid crystal matrix in an aqueous medium. And, saturated fatty acids having 14 to 20 carbon is atoms ($C_{14}$~$C_{20}$) exist in a solid form at room temperature and show high viscosity when prepared into a pre-concentrate, which leads to low injectability. However, it has been found by the present invention that unsaturated fatty acids having 14 to 20 carbon atoms ($C_{14}$~$C_{20}$) exist in a liquid form at room temperature and show high liquid crystal matrix forming ability in an aqueous medium. In terms of excellent biocompatibility and liquid crystal forming ability, the unsaturated fatty acid having 14 to 20 carbon atoms ($C_{14}$~$C_{20}$) may be preferably oleic acid, linoleic acid, myristoleic acid, palmitoleic acid, 11-eicosenoic acid, or a mixture thereof, more preferably oleic acid, linoleic acid, or a mixture thereof, and still more preferably oleic acid. The unsaturated fatty acid having 14 to 20 carbon atoms ($C_{14}$~$C_{20}$), which is an unsaturated fatty acid having one or two double bonds, is a component derived from the body which is widely present in animals and plants and has excellent biocompatibility and biodegradability. The unsaturated fatty acid having 14 to 20 carbon atoms ($C_{14}$~$C_{20}$), including oleic acid, linoleic acid, myristoleic acid, palmitoleic acid, and 11-eicosenoic acid, rapidly forms a lipid solution having low-viscosity, thereby being able to provide excellent injectability. That is, when the pre-concentrate of the present invention is contacted with an excess of aqueous phase, it is possible to form a robust liquid crystal matrix within 1 hour, preferably within about 30 minutes. In addition, the pre-concentrate of the present invention have a low viscosity (e.g., 1500 mPa·s or less, preferably 1000 mPa·s or less) at room temperature (about 25° C.), so that they can be easily introduced into a living body through a 24 to 26 gauge syringe. The unsaturated fatty acid having 14 to 20 carbon atoms ($C_{14}$~$C_{20}$) may be present in an amount ranging from 30 to 70 wt % based on the total weight thereof. When the amount of the unsaturated fatty acid is less than 30 wt % or exceeds 70 wt % based on the total weight of the pre-concentrate, the liquid crystal forming ability may be significantly reduced when injected into the living body and the sustained release ability of the active ingredient may be lowered; and thus it may be difficult to show the release-controlling ability for more than a week.

The phospholipid, together with the unsaturated fatty acid having 14 to 20 carbon atoms ($C_{14}$~$C_{20}$), plays a role in forming a liquid crystal matrix having pores in nanometer units that can serve as a drug-depot in an aqueous medium, and plays a role in helping the solubilization of a pharmacologically active substance. The phospholipid, which contains a polar head group and two nonpolar tail groups, includes variously-derived or synthetic phospholipids, such as phospholipids derived from soybean or egg yolk. The phospholipid may be phosphatidylcholine, phosphatidylethanolamine, phosphatidylserine, phosphatidylglycerol, or a synthetic derivative thereof (e.g., dipalmitoylphosphatidylcholine, distearoylphosphatidylcholine, etc.), and include a mixture of one or more thereof. Preferably, the phospholipid may be phosphatidylcholine derived from egg yolk or soybean. The phospholipid may be present in an amount ranging from 25 to 50 wt % based on the total weight thereof. When the amount of the phospholipid is less than 25 wt % based on the total weight of the pre-concentrate, it may be difficult to form a liquid crystal upon injection into the body, and the ability to control extended release may be reduced. When the amount of the phospholipid exceeds 50 wt % based on the total weight of the pre-concentrate, the ability to form a liquid crystal may be also lowered and the ability to control drug release may be deteriorated due to formation of lamellar spheres.

The α-tocopherol acetate helps to keep the internal structure of the liquid crystal strong (i.e., stiffening), and plays a role in delaying the release rate of a pharmacologically active substance. The α-tocopherol acetate includes D-α-tocopherol acetate, DL-α-tocopherol acetate, or a mixture thereof. The α-tocopherol acetate may be present in an amount ranging from 5 to 20 wt % based on the total weight thereof.

The pre-concentrate of the present invention may further comprise a biocompatible solvent, if necessary. The biocompatible solvent includes a solvent that can be introduced into the human body in the form of an injectable formulation, for example, one or more organic solvents selected from the group consisting of ethanol, propylene glycol, N-methylpyrrolidone, and benzyl alcohol; or an aqueous solution of the organic solvent, but not limited thereto. Preferably, the biocompatible solvent may be ethanol or an aqueous solution of ethanol. The biocompatible solvent serves to improve solubilization or injectability of an active ingredient. When the pre-concentrate containing a biocompatible solvent is injected into the body, the solvent will be diluted and removed by the biological fluid during the formation of a liquid crystal in the form of a sustained-release depot. The biocompatible solvent may be present in an amount ranging from 5 to 10 wt % based on the total weight thereof. In an embodiment, the pre-concentrate of the present invention may comprise 30 to 65 wt % of the unsaturated fatty acid having 14 to 20 carbon atoms ($C_{14}$~$C_{20}$); 25 to 50 wt % of the phospholipid; 5 to 20 wt % of α-tocopherol acetate; and 5 to 10 wt % of the biocompatible solvent.

The pre-concentrate of the present invention may further comprise a medium-chain triglyceride, if necessary. The medium chain triglyceride helps to maintain the internal structure of the liquid crystal, and also serves to further lower the viscosity of the pre-concentrate and the pharmaceutical composition comprising the same. The medium chain triglyceride is composed of 3 molecules of fatty acids having 6 or 12 carbon atoms and 1 molecule of glycerol. The medium chain triglyceride includes, for example, tricaproin, tricaprylin, tricaprin, trilaurin, or a mixture thereof, but not limited thereto. The medium chain triglyceride may be present in an amount ranging from 1 to 5 wt % based on the total weight thereof. In an embodiment, the pre-concentrate of the present invention may comprise 30 to 65 wt % of the unsaturated fatty acid having 14 to 20 carbon atoms ($C_{14}$~$C_{20}$); 25 to 50 wt % of the phospholipid; 5 to 20 wt % of α-tocopherol acetate; and 1 to 5 wt % of the medium chain triglyceride. In another embodiment, the pre-concentrate of the present invention may comprise 30 to 55 wt % of the unsaturated fatty acid having 14 to 20 carbon atoms ($C_{14}$~$C_{20}$); 25 to 45 wt % of the phospholipid; 5 to 20 wt % of α-tocopherol acetate; 1 to 5 wt % of the medium chain triglyceride; and 5 to 10 wt % of the biocompatible solvent.

The pre-concentrate of the present invention does not comprise diacyl glycerol and sorbitan unsaturated fatty acid ester. Examples of the diacyl glycerol include glyceryl dipalmitate, glyceryl phytanoate, glyceryl palmitoleate, glyceryl distearate, glyceryl dioleate, glceryl dielaidiate, glyceryl dilinoleate, and the like. Examples of the sorbitan unsaturated fatty acid ester include sorbitan monooleate, sorbitan monolinoleate, sorbitan monopalmitoleate, sorbitan monomyristoleate, sorbitan sesquioleate, sorbitan sesquilinoleate, sorbitan sesquipalmitoleate, sorbitan sesquimyristoleate, sorbitan dioleate, sorbitan dilinoleate, sorbitan dipalmitoleate, sorbitan dimyristoleate, and the like. The pre-concentrate of the present invention does not contain any of the above-mentioned diacyl glycerol and sorbitan unsaturated fatty acid ester.

The present invention also provides a sustained-release injectable pharmaceutical composition in the form of a lipid solution, comprising a pharmacologically active substance; and the pre-concentrate, wherein the sustained-release injectable pharmaceutical composition is free of diacyl glycerol and sorbitan unsaturated fatty acid ester.

In the pharmaceutical composition of the present invention, the pharmacologically active substance (active pharmaceutical ingredient) may be a drug having a solubility of 0.1 mg/ml or more in the pre-concentrate. The pharmacologically active substance having a solubility of less than 0.1 mg/ml in the pre-concentrate leads to the increase in injection volume of the sustained-release injectable formulation and thus may induce high injection pain and be difficult to prepare a sustained-release formulation. Examples of the pharmacologically active substance having a solubility of 0.1 mg/ml or more in the pre-concentrate include leuprolide or a pharmaceutically acceptable salt thereof (e.g., leuprolide acetate); goserelin or a pharmaceutically acceptable salt thereof (e.g., goserelin acetate); entecavir (including monohydrate thereof) or a pharmaceutically acceptable salt thereof; a somatostatin analogue (e.g., octreotide, lanreotide, and pasireotide) or a pharmaceutically acceptable salt thereof; a glucagon-like peptide-1 (GLP-1) analogue (e.g., exenatide, liraglutide, albiglutide, lixisenatide and semaglutide) or a pharmaceutically acceptable salt thereof; dutasteride to or a pharmaceutically acceptable salt thereof; donepezil or a pharmaceutically acceptable salt thereof; aripiprazole or a pharmaceutically acceptable salt thereof; paliperidone or a pharmaceutically acceptable salt thereof; or risperidone or a pharmaceutically acceptable salt thereof, and the like, but not limited thereto. In an embodiment, the pharmacologically active substance may be gonadotropin-releasing is hormone (GnRH) derivative, for example, leuprolide or a pharmaceutically acceptable salt thereof (e.g., leuprolide acetate); or goserelin or a pharmaceutically acceptable salt thereof (e.g., goserelin acetate). The pharmacologically active substance may be included in a therapeutically effective amount in the pharmaceutical composition of the present invention. For example, the pharmacologically active substance may be included in an amount ranging from 0.1 to 10 wt %, preferably from 0.9 to 7 wt %, based on the total weight of the composition.

In an embodiment, the pharmaceutical composition of the present invention comprises 0.1 to 10 wt % of the pharmacologically active substance; 30 to 60 wt % of the unsaturated fatty acid having 14 to 20 carbon atoms ($C_{14}$~$C_{20}$); 25 to 50 wt % of the phospholipid; and 5 to 20 wt % of α-tocopherol acetate. In another embodiment, the pharmaceutical composition of the present invention comprises 0.1 to 10 wt % of the pharmacologically active substance; 30 to 60 wt % of the unsaturated fatty acid having 14 to 20 carbon atoms ($C_{14}$~$C_{20}$); 25 to 45 wt % of the phospholipid; 5 to 20 wt % of α-tocopherol acetate; and 5 to 10 wt % of the biocompatible solvent. In still another embodiment, the pharmaceutical composition of the present invention comprises 0.1 to 10 wt % of the pharmacologically active substance; 30 to 55 wt % of the unsaturated fatty acid having 14 to 20 carbon atoms ($C_{14}$~$C_{20}$); 25 to 45 wt % of the phospholipid; 5 to 20 wt % of α-tocopherol acetate; 1 to 5 wt % of the medium chain triglyceride; and 5 to 10 wt % of the biocompatible solvent.

The sustained-release lipid pre-concentrate in the form of a lipid solution according to the present invention; and the sustained-release injectable pharmaceutical composition in the form of a lipid solution comprising the same may be subjected to a conventional sterile process, for example, sterile filtration using a membrane filter.

The present invention will be described in further detail with reference to the following examples and experimental examples. These examples and experimental examples are for illustrative purposes only and are not intended to limit the scope of the present invention.

Examples 1 to 119. Preparation of Sustained-Release Lipid Pre-Concentrates

Sustained-release lipid pre-concentrates were prepared according to the components and amounts shown in Tables 1 to 7. The amounts of Tables 1 to 7 represent the weight percent (wt %) of each component in the sustained-release lipid pre-concentrate. Specifically, soybean-derived phosphatidylcholine or phosphatidylethanolamine, unsaturated fatty acid having 14 to 20 carbon atoms ($C_{14}$~$C_{20}$) (oleic acid, linoleic acid, myristoleic acid, palmitoleic acid, or 11-eicosenoic acid), DL-α-tocopherol acetate, medium chain triglyceride [Kollisolv™ MCT 70 (a mixture of tricapryline and tricaprine, about 68:32 of weight ratio), BASF], and/or biocompatible solvent (ethanol, propylene glycol, or N-methylpyrrolidone) were added to a glass vial; and then mixed under stirring at room temperature with a magnetic stirrer. Each resulting mixture was homogenized at room temperature with a homogenizer (POLYTRON PT1200E, KINEMATICA) under the condition of about 5,000 rpm for about 5 minutes, and then left at room temperature for about 3 hours to prepare each sustained-release lipid pre-concentrate. The total batch size thereof was prepared in 20 g per pre-concentrate.

TABLE 1

| | Example | | | | | | | | | | | | | | | | | | | |
|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 |
| Oleic acid | 30 | 40 | 55 | 65 | 70 | 30 | 40 | 55 | 65 | 30 | 40 | 55 | 65 | 35 | 35 | 45 | 45 | 55 | 55 | 55 |
| Phosphatidylcholine | 50 | 45 | 35 | 30 | 25 | 50 | 45 | 35 | 25 | 50 | 45 | 35 | 25 | 45 | 45 | 35 | 35 | 35 | 35 | 35 |
| DL-α-Tocopherol acetate | 20 | 15 | 10 | 5 | 5 | 15 | 10 | 5 | 5 | 15 | 10 | 5 | 5 | 10 | 8 | 10 | 8 | 4 | 2.5 | 1 |
| Medium chain triglyceride | | | | | | 5 | 5 | 5 | 5 | | | | | 5 | 2 | 5 | 2 | 1 | 2.5 | 4 |
| Ethanol | | | | | | | | | | 5 | 5 | 5 | 5 | 5 | 10 | 5 | 10 | 5 | 5 | 5 |

TABLE 2

| | Example | | | | | | | | | | | | | |
|---|---|---|---|---|---|---|---|---|---|---|---|---|---|---|
| | 21 | 22 | 23 | 24 | 25 | 26 | 27 | 28 | 29 | 30 | 31 | 32 | 33 | 34 |
| Oleic acid | 35 | 35 | 45 | 45 | 55 | 55 | 55 | 35 | 35 | 45 | 45 | 55 | 55 | 55 |
| Phosphatidylcholine | 45 | 45 | 35 | 35 | 35 | 35 | 35 | 45 | 45 | 35 | 35 | 35 | 35 | 35 |
| DL-α-Tocopherol acetate | 10 | 8 | 10 | 8 | 4 | 2.5 | 1 | 10 | 8 | 10 | 8 | 4 | 2.5 | 1 |
| Medium chain triglyceride | 5 | 2 | 5 | 2 | 1 | 2.5 | 4 | 5 | 2 | 5 | 2 | 1 | 2.5 | 4 |
| Propylene glycol | 5 | 10 | 5 | 10 | 5 | 5 | 5 | | | | | | | |
| N-methylpyrrolidone | | | | | | | | 5 | 10 | 5 | 10 | 5 | 5 | 5 |

TABLE 3

| | Example | | | | | | | | | | | | | | | | |
|---|---|---|---|---|---|---|---|---|---|---|---|---|---|---|---|---|---|
| | 35 | 36 | 37 | 38 | 39 | 40 | 41 | 42 | 43 | 44 | 45 | 46 | 47 | 48 | 49 | 50 | 51 |
| Linoleic acid | 30 | 40 | 55 | 65 | 70 | 30 | 40 | 55 | 65 | 30 | 40 | 55 | 65 | 35 | 35 | 45 | 45 |
| Phosphatidylcholine | 50 | 45 | 35 | 30 | 25 | 50 | 45 | 35 | 25 | 50 | 45 | 35 | 25 | 45 | 45 | 35 | 35 |
| DL-α-Tocopherol acetate | 20 | 15 | 10 | 5 | 5 | 15 | 10 | 5 | 5 | 15 | 10 | 5 | 5 | 10 | 8 | 10 | 8 |
| Medium chain triglyceride | | | | | | 5 | 5 | 5 | 5 | | | | | 5 | 2 | 5 | 2 |
| Ethanol | | | | | | | | | | 5 | 5 | 5 | 5 | 5 | 10 | 5 | 10 |

TABLE 4

| | Example | | | | | | | | | | | | | | | | |
|---|---|---|---|---|---|---|---|---|---|---|---|---|---|---|---|---|---|
| | 52 | 53 | 54 | 55 | 56 | 57 | 58 | 59 | 60 | 61 | 62 | 63 | 64 | 65 | 66 | 67 | 68 |
| Myristoleic acid | 30 | 40 | 55 | 65 | 70 | 30 | 40 | 55 | 65 | 30 | 40 | 55 | 65 | 35 | 35 | 45 | 45 |
| Phosphatidylcholine | 50 | 45 | 35 | 30 | 25 | 50 | 45 | 35 | 25 | 50 | 45 | 35 | 25 | 45 | 45 | 35 | 35 |
| DL-α-Tocopherol acetate | 20 | 15 | 10 | 5 | 5 | 15 | 10 | 5 | 5 | 15 | 10 | 5 | 5 | 10 | 8 | 10 | 8 |
| Medium chain triglyceride | | | | | | 5 | 5 | 5 | 5 | | | | | 5 | 2 | 5 | 2 |
| Ethanol | | | | | | | | | | 5 | 5 | 5 | 5 | 5 | 10 | 5 | 10 |

TABLE 5

| | Example | | | | | | | | | | | | | | | | |
|---|---|---|---|---|---|---|---|---|---|---|---|---|---|---|---|---|---|
| | 69 | 70 | 71 | 72 | 73 | 74 | 75 | 76 | 77 | 78 | 79 | 80 | 81 | 82 | 83 | 84 | 85 |
| Palmitoleic acid | 30 | 40 | 55 | 65 | 70 | 30 | 40 | 55 | 65 | 30 | 40 | 55 | 65 | 35 | 35 | 45 | 45 |
| Phosphatidylcholine | 50 | 45 | 35 | 30 | 25 | 50 | 45 | 35 | 25 | 50 | 45 | 35 | 25 | 45 | 45 | 35 | 35 |
| DL-α-Tocopherol acetate | 20 | 15 | 10 | 5 | 5 | 15 | 10 | 5 | 5 | 15 | 10 | 5 | 5 | 10 | 8 | 10 | 8 |
| Medium chain triglyceride | | | | | | 5 | 5 | 5 | 5 | | | | | 5 | 2 | 5 | 2 |
| Ethanol | | | | | | | | | | 5 | 5 | 5 | 5 | 5 | 10 | 5 | 10 |

TABLE 6

| | Example | | | | | | | | | | | | | | | | |
|---|---|---|---|---|---|---|---|---|---|---|---|---|---|---|---|---|---|
| | 86 | 87 | 88 | 89 | 90 | 91 | 92 | 93 | 94 | 95 | 96 | 97 | 98 | 99 | 100 | 101 | 102 |
| 11-Eicosenoic acid | 30 | 40 | 55 | 65 | 70 | 30 | 40 | 55 | 65 | 30 | 40 | 55 | 65 | 35 | 35 | 45 | 45 |
| Phosphatidylcholine | 50 | 45 | 35 | 30 | 25 | 50 | 45 | 35 | 25 | 50 | 45 | 35 | 25 | 45 | 45 | 35 | 35 |
| DL-α-Tocopherol acetate | 20 | 15 | 10 | 5 | 5 | 15 | 10 | 5 | 5 | 15 | 10 | 5 | 5 | 10 | 8 | 10 | 8 |
| Medium chain triglyceride | | | | | | 5 | 5 | 5 | 5 | | | | | 5 | 2 | 5 | 2 |
| Ethanol | | | | | | | | | | 5 | 5 | 5 | 5 | 5 | 10 | 5 | 10 |

TABLE 7

| | Example | | | | | | | | | | | | | | | | |
|---|---|---|---|---|---|---|---|---|---|---|---|---|---|---|---|---|---|
| | 103 | 104 | 105 | 106 | 107 | 108 | 109 | 110 | 111 | 112 | 113 | 114 | 115 | 116 | 117 | 118 | 119 |
| Oleic acid | 30 | 40 | 55 | 65 | 70 | 30 | 40 | 55 | 65 | 30 | 40 | 55 | 65 | 35 | 35 | 45 | 45 |
| Phosphatidyl-ethanolamine | 50 | 45 | 35 | 30 | 25 | 50 | 45 | 35 | 25 | 50 | 45 | 35 | 25 | 45 | 45 | 35 | 35 |
| DL-α-Tocopherol acetate | 20 | 15 | 10 | 5 | 5 | 15 | 10 | 5 | 5 | 15 | 10 | 5 | 5 | 10 | 8 | 10 | 8 |
| Medium chain triglyceride | | | | | | 5 | 5 | 5 | 5 | | | | | 5 | 2 | 5 | 2 |
| Ethanol | | | | | | | | | | 5 | 5 | 5 | 5 | 5 | 10 | 5 | 10 |

Examples 120 to 123. Preparation of the Sustained-Release Injectable Pharmaceutical Composition in the Form of a Lipid Solution Containing Leuprolide Acetate Sustained-release injectable pharmaceutical compositions in the form of a lipid solution containing leuprolide acetate were prepared according to the components and amounts shown in Table 8. The amounts of Table 8 represent the weight percent (wt %) of each component in the pharmaceutical composition. Specifically, to phosphatidylcholine, oleic acid, DL-α-tocopherol acetate, medium chain triglyceride [Kollisolv™ MCT 70 (a mixture of tricapryline and tricaprine, about 68:32 of weight ratio), BASF], and/or an aqueous solution of ethanol (ethanol:water for injection=4.81 mg:2.89 mg) were added to a glass vial; and then mixed under stirring at room temperature with a magnetic stirrer. Each resulting mixture was homogenized at room temperature with a homogenizer (POLYTRON PT1200E, KINEMATICA) under the condition of about 5,000 rpm for about 5 minutes. Leuprolide acetate was added to each mixture, which was homogenized at room temperature with a homogenizer under the condition of about 3,000 rpm for about 10 minutes and then left at room temperature for about 3 hours to prepare the sustained-release injectable pharmaceutical compositions in the form of a lipid solution.

TABLE 8

| | Example | | | |
|---|---|---|---|---|
| | 120 | 121 | 122 | 123 |
| Oleic acid | 40.54 | 36.04 | 36.04 | 31.53 |
| Phosphatidylcholine | 41.58 | 41.58 | 41.58 | 41.58 |
| DL-α-Tocopherol acetate | 6.43 | 9.01 | 10.93 | 15.44 |
| Medium chain triglyceride | | 1.92 | | |
| Ethanol | 4.81 | 4.81 | 4.81 | 4.81 |
| Water for injection | 2.89 | 2.89 | 2.89 | 2.89 |
| Leuprolide acetate | 3.75 | 3.75 | 3.75 | 3.75 |

Examples 124 to 126. Preparation and Evaluation of the Sustained-Release Injectable Pharmaceutical Composition in the Form of a Lipid Solution Containing Goserelin Acetate Sustained-release injectable pharmaceutical compositions in the form of a lipid solution containing goserelin acetate were prepared according to the components and amounts shown in Table 9. The amounts of Table 9 represent the weight percent (wt %) of each component in the pharmaceutical composition. Specifically, to phosphatidylcholine, oleic acid, DL-α-tocopherol acetate, medium chain triglyceride [Kollisolv™ MCT 70 (a mixture of tricapryline and tricaprine, about 68:32 of weight ratio), BASF], and/or an aqueous solution of ethanol (ethanol:water for injection=5.56 mg:4.00 mg or 5.76 mg:4.14 mg) were added to a glass vial; and then mixed under stirring at room temperature with a magnetic stirrer. Each resulting mixture was homogenized is at room temperature with a homogenizer (POLYTRON PT1200E, KINEMATICA) under the condition of about 5,000 rpm for about 5 minutes. Goserelin acetate was added to each mixture, which was homogenized at room temperature with a homogenizer under the condition of about 3,000 rpm for about 10 minutes and then left at room temperature for about 3 hours to prepare the sustained-release injectable pharmaceutical compositions in the form of a lipid solution.

TABLE 9

|  | Example | | |
|---|---|---|---|
|  | 124 | 125 | 126 |
| Oleic acid | 36.04 | 36.04 | 36.15 |
| Phosphatidylcholine | 41.58 | 41.58 | 41.90 |
| DL-α-Tocopherol acetate | 9.01 | 10.93 | 11.08 |
| Medium chain triglyceride | 1.92 |  |  |
| Ethanol | 5.56 | 5.56 | 5.76 |
| Water for injection | 4.00 | 4.00 | 4.14 |
| Goserelin acetate | 1.89 | 1.89 | 0.97 |

Examples 127 to 130. Preparation and Evaluation of the Sustained-Release Injectable Pharmaceutical Composition in the Form of a Lipid Solution Containing Liraglutide Sustained-release injectable pharmaceutical compositions in the form of a lipid solution containing liraglutide were prepared according to the components and amounts shown in Table 10. The amounts of Table 10 represent the weight percent (wt %) of each component in the pharmaceutical composition. Specifically, phosphatidylcholine, to oleic acid, DL-α-tocopherol acetate, medium chain triglyceride [Kollisolv™ MCT 70 (a mixture of tricapryline and tricaprine, about 68:32 of weight ratio), BASF], and/or an aqueous solution of ethanol (ethanol:water for injection=4.65 mg:3.05 mg) were added to a glass vial; and then mixed under stirring at room temperature with a magnetic stirrer. Each resulting mixture was homogenized at room temperature with a is homogenizer (POLYTRON PT1200E, KINEMATICA) under the condition of about 5,000 rpm for about 5 minutes. Liraglutide was added to each mixture, which was homogenized at room temperature with a homogenizer under the condition of about 3,000 rpm for about 10 minutes and then left at room temperature for about 3 hours to prepare the sustained-release injectable pharmaceutical compositions in the form of a lipid solution.

TABLE 10

|  | Example | | | |
|---|---|---|---|---|
|  | 127 | 128 | 129 | 130 |
| Oleic acid | 40.54 | 36.04 | 36.04 | 31.53 |
| Phosphatidylcholine | 39.33 | 39.33 | 39.33 | 39.33 |

TABLE 10-continued

|  | Example | | | |
|---|---|---|---|---|
|  | 127 | 128 | 129 | 130 |
| DL-α-Tocopherol acetate | 6.43 | 9.01 | 10.93 | 15.44 |
| Medium chain triglyceride |  | 1.92 |  |  |
| Ethanol | 4.65 | 4.65 | 4.65 | 4.65 |
| Water for injection | 3.05 | 3.05 | 3.05 | 3.05 |
| Liraglutide | 6.00 | 6.00 | 6.00 | 6.00 |

Examples 131 to 134. Preparation and Evaluation of the Sustained-Release Injectable Pharmaceutical Composition in the Form of a Lipid Solution Containing Dutasteride Sustained-release injectable pharmaceutical compositions in the form of a lipid solution containing dutasteride were prepared according to the components and amounts shown in Table 11. The amounts of Table 11 represent the weight percent (wt %) of each component in the pharmaceutical composition. Specifically, to phosphatidylcholine, oleic acid, DL-α-tocopherol acetate, medium chain triglyceride [Kollisolv™ MCT 70 (a mixture of tricapryline and tricaprine, about 68:32 of weight ratio), BASF], and/or ethanol were added to a glass vial; and then mixed under stirring at room temperature with a magnetic stirrer. Each resulting mixture was homogenized at room temperature with a homogenizer (POLYTRON PT1200E, KINEMATICA) under the is condition of about 5,000 rpm for about 5 minutes. Dutasteride was added to each mixture, which was homogenized at room temperature with a homogenizer under the condition of about 3,000 rpm for about 20 minutes and then left at room temperature for about 3 hours to prepare the sustained-release injectable pharmaceutical compositions in the form of a lipid solution.

TABLE 11

|  | Example | | | |
|---|---|---|---|---|
|  | 131 | 132 | 133 | 134 |
| Oleic acid | 49.0 | 44.0 | 42.0 | 36.0 |
| Phosphatidylcholine | 40.2 | 40.2 | 40.2 | 40.2 |
| DL-α-Tocopherol acetate | 5.0 | 8.0 | 12.0 | 18.0 |
| Medium chain triglyceride |  | 2.0 |  |  |
| Ethanol | 5.0 | 5.0 | 5.0 | 5.0 |
| Dutasteride | 0.8 | 0.8 | 0.8 | 0.8 |

Examples 135 to 136. Preparation and Evaluation of the Sustained-Release Injectable Pharmaceutical Composition in the Form of a Lipid Solution Containing Paliperidone Sustained-release injectable pharmaceutical compositions in the form of a lipid solution containing paliperidone were prepared according to the components and amounts shown in Table 12. The amounts of Table 12 represent the weight percent (wt %) of each component in the pharmaceutical composition. Specifically, to phosphatidylcholine, oleic acid, DL-α-tocopherol acetate, medium chain triglyceride [Kollisolv™ MCT 70 (a mixture of tricapryline and tricaprine, about 68:32 of weight ratio), BASF], ethanol and benzyl alcohol were added to a glass vial; and then mixed under stirring at room temperature with a magnetic stirrer.

Each resulting mixture was homogenized at room temperature with a homogenizer (POLYTRON PT1200E, KINEMATICA) under the condition of about 5,000 rpm for about 5 minutes. Paliperidone was added to each mixture, which was homogenized at room temperature with a homogenizer under the condition of about 3,000 rpm for about 20 minutes and then left at room temperature for about 3 hours to prepare the sustained-release injectable pharmaceutical compositions in the form of a lipid solution.

TABLE 12

|  | Example | |
| --- | --- | --- |
|  | 135 | 136 |
| Oleic acid | 51.0 | 51.0 |
| Phosphatidylcholine | 30.0 | 28.0 |
| DL-α-Tocopherol acetate | 5.0 | 5.0 |
| Medium chain triglyceride | 1.0 | 1.0 |
| Ethanol | 3.0 | 5.0 |
| Benzyl alcohol | 2.0 | 2.0 |
| Paliperidone | 8.0 | 8.0 |

Comparative Examples 1 to 8. Preparation of Sustained-Release Lipid Pre-Concentrates Sustained-release lipid pre-concentrates were prepared according to the components and amounts shown in Tables 13 and 14. The amounts of Tables 13 and 14 represent the weight percent (wt %) of each component in the sustained-release lipid pre-concentrate. The sustained-release lipid pre-concentrates of Comparative Examples 1 to 4 were prepared in the same manner as in Examples 1 to 20, using to glyceryl dioleate instead of oleic acid, according to the components and amounts of Table 13. And, the sustained-release lipid pre-concentrates of Comparative Examples 5 to 8 were prepared in the same manner as in Examples 1 to 20, using sorbitan monooleate instead of oleic acid, according to the components and amounts of Table 14.

TABLE 13

|  | Comparative Example | | | |
| --- | --- | --- | --- | --- |
|  | 1 | 2 | 3 | 4 |
| Glyceryl dioleate | 35 | 45 | 35 | 35 |
| Phosphatidylcholine | 45 | 35 | 45 | 45 |
| DL-α-Tocopherol acetate | 15 | 15 | 10 | 8 |
| Medium chain triglyceride |  |  | 5 | 2 |
| Ethanol | 5 | 5 | 5 | 10 |

TABLE 14

|  | Comparative Example | | | |
| --- | --- | --- | --- | --- |
|  | 5 | 6 | 7 | 8 |
| Sorbitan monooleate | 35 | 45 | 35 | 35 |
| Phosphatidylcholine | 45 | 35 | 45 | 45 |
| DL-α-Tocopherol acetate | 15 | 15 | 10 | 8 |
| Medium chain triglyceride |  |  | 5 | 2 |
| Ethanol | 5 | 5 | 5 | 10 |

Experimental Example 1. Evaluation of Injectability of Sustained-Release Lipid Pre-Concentrates In order to evaluate the injectability of the sustained-release lipid pre-concentrates prepared in Examples 1 to 20 and Comparative Examples 1 to 8, the viscosity of each sustained-release lipid pre-concentrate was measured using a cone-plate rotating to viscometer (RM-100 touch, Ramy). The results of Examples 14 and 15 and Comparative Examples 3, 4, 7 and 8 are shown in FIG. 1. As can be seen from the above results, the sustained-release lipid pre-concentrate containing sorbitan monooleate showed about 5~10 times higher viscosities, in comparison with the sustained-release pre-concentrate containing oleic acid or glyceryl dioleate, and thus exhibited remarkably low injectability. In addition, the sustained-release lipid pre-concentrates containing oleic acid showed lower viscosities under the same condition, in comparison with the sustained-release lipid pre-concentrates containing glyceryl dioleate, and thus exhibited the most excellent injectability.

Figure 2A:
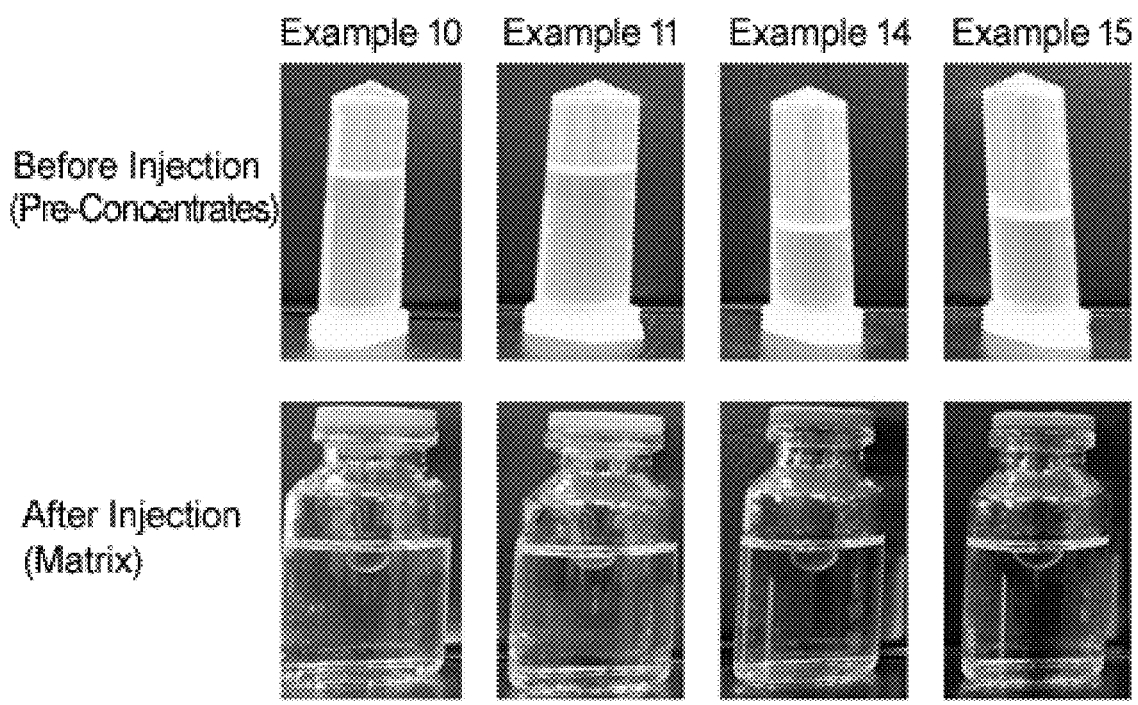
FIGS. 2a to 2c show the appearances of the pre-concentrates prepared in Examples 10, 11, 14 and 15 (FIG. 2a), Comparative Examples 1 to 4 (FIG. 2b), Comparative Examples 5 to 8 (FIG. 2c), when those were filled in a 1 ml syringe and is then injected into 10 ml of pH 7.4 phosphate buffer through a 26 gauge needle.
Figure 2B:
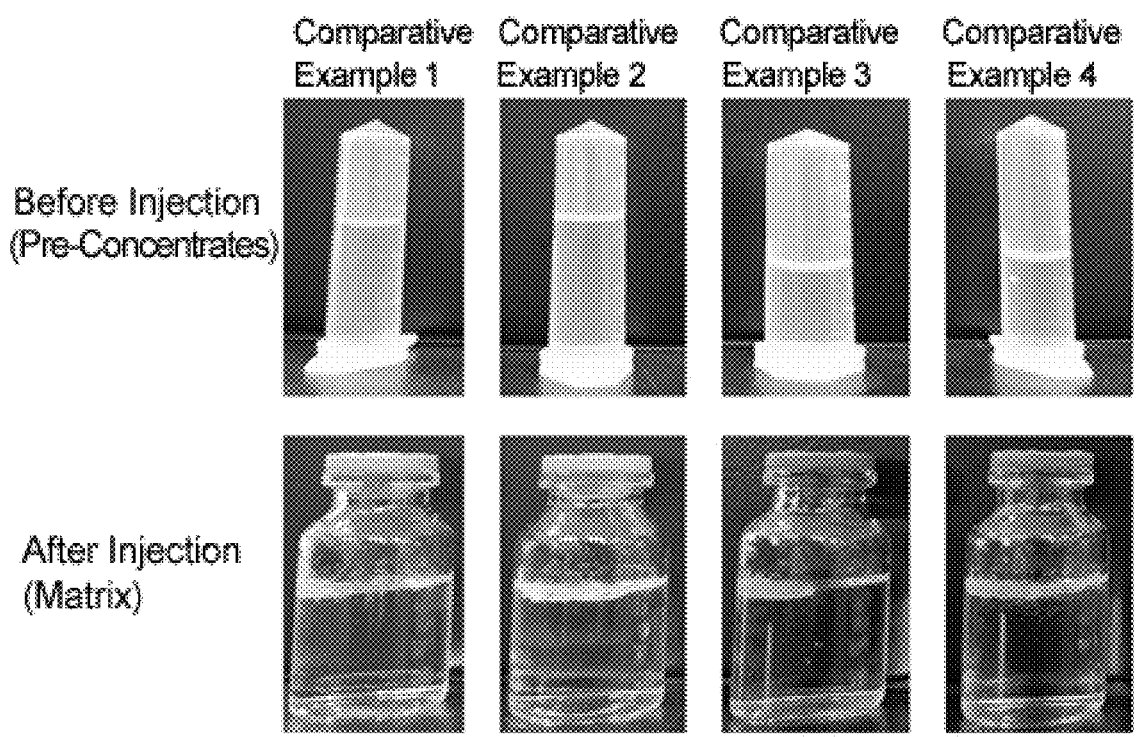
Figure 2C:
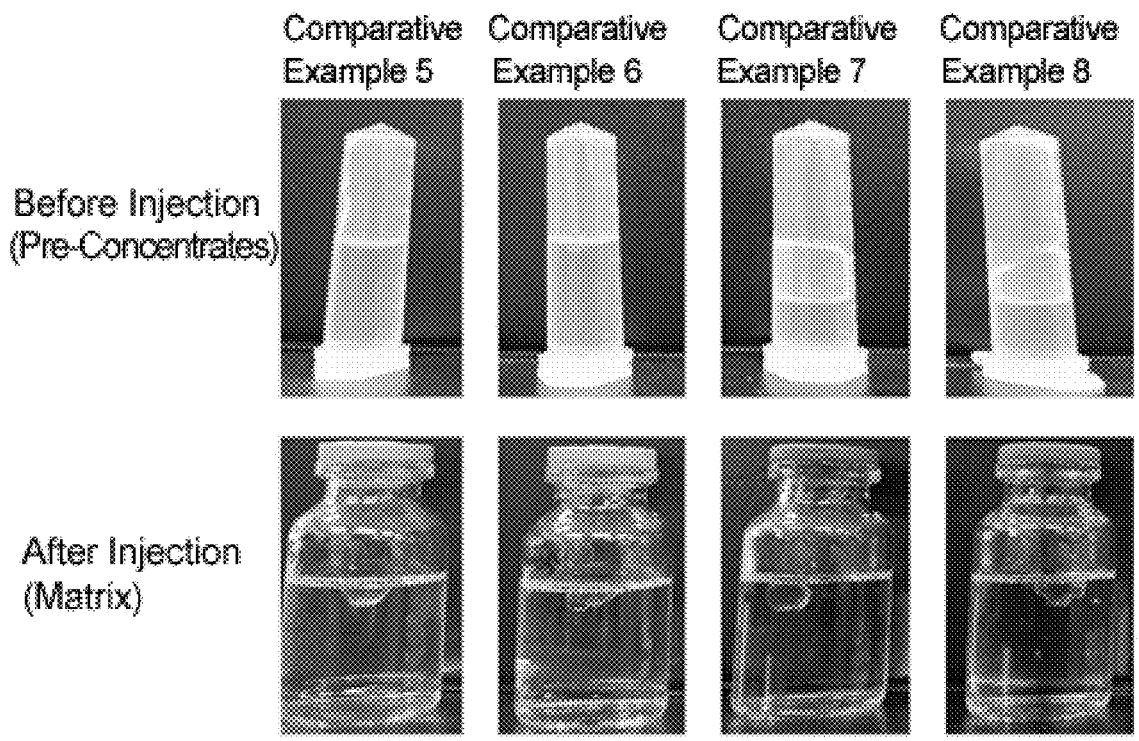

Experimental Example 2. Evaluation of Matrix-Forming Ability of Sustained-Release Lipid Pre-Concentrates in Aqueous Phase The sustained-release lipid pre-concentrates prepared in Examples 10, 11, 14 and 15 and Comparative Examples 1 to 8 were filled in a 1 ml syringe and injected into 10 ml of pH 7.4 phosphate buffer through a 26 gauge needle. The resulting appearances thereof are shown in FIGS. 2a to 2c. As can be seen from the results of FIG. 2, all of the sustained-release lipid pre-concentrates were in the form of a fluidal lipid solution at room temperature before exposure to the aqueous phase; and formed a liquid crystal matrix when injected into the aqueous phase. However, in contrast to the sustained-release lipid pre-concentrates containing glyceryl dioleate (the pre-concentrates of Comparative Examples 1 to 4), the sustained-release lipid pre-concentrates containing oleic acid (the pre-concentrates of Examples 10, 11, 14 and 15) and the sustained-release lipid pre-concentrates containing sorbitan monooleate (the pre-concentrates of Comparative Examples 5 to 8) formed an ideal spherical liquid crystal matrix, thereby exhibiting excellent matrix (liquid crystal)-forming ability.

Figure 3:
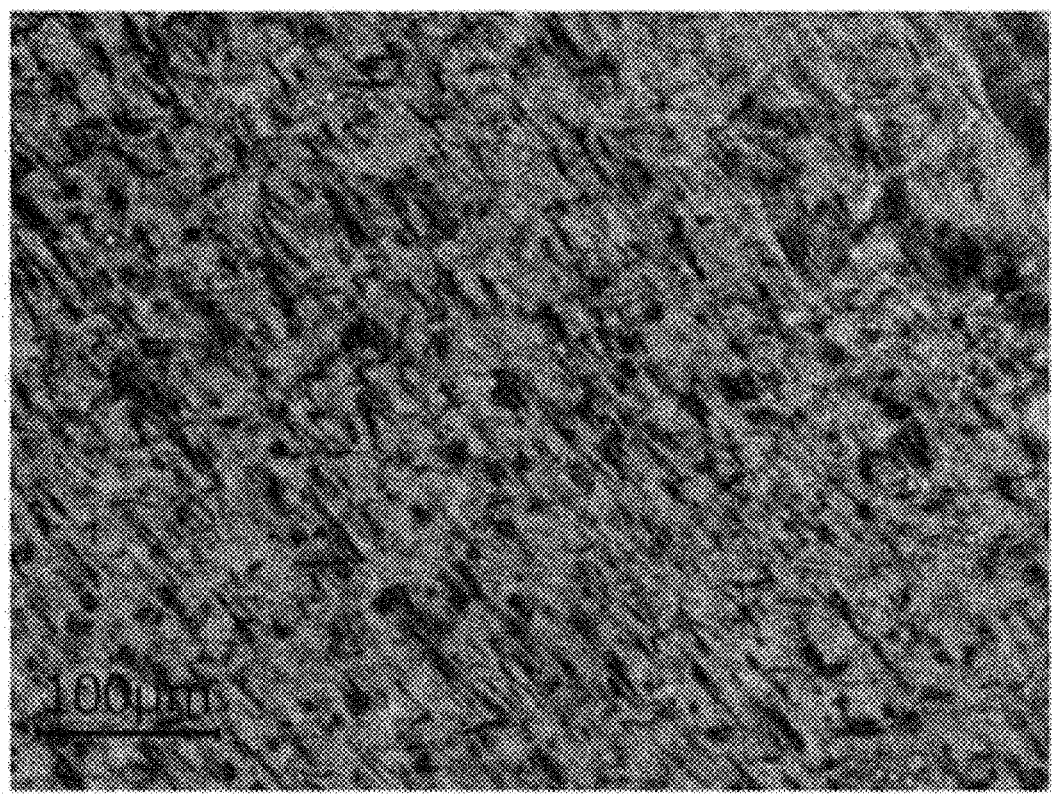
FIG. 3 shows the results (250 magnification) obtained by analyzing with a polarizing microscope the structure of the liquid crystal formed by injecting the pre-concentrate prepared in Example 15 into an excess of aqueous phase.

Experimental Example 3. Confirmation of Liquid Crystal Structure within the Matrix of Sustained-Release Lipid Pre-Concentrates in Aqueous Phase 20 μl of the sustained-release lipid pre-concentrate prepared in Example 15 was thinly applied to a slide glass, and then placed in a petri dish containing 20 ml of pH 7.4 phosphate buffer and left at room temperature for about 3 hours. In order to confirm the liquid crystal structure formed by exposure to the aqueous phase, the water on the slide glass was carefully removed and a cover glass was covered so that no air bubbles were generated, and then it was observed at 250 magnification using a polarizing microscope (S38, MIC). The result thereof is shown in FIG. 3. From the result of FIG. 3, it can be confirmed that the sustained-release lipid pre-concentrate prepared according to the present invention forms a reversed hexagonal phase that enables sustained release of the pharmacologically active substance upon exposure to an aqueous phase.

Figure 4:
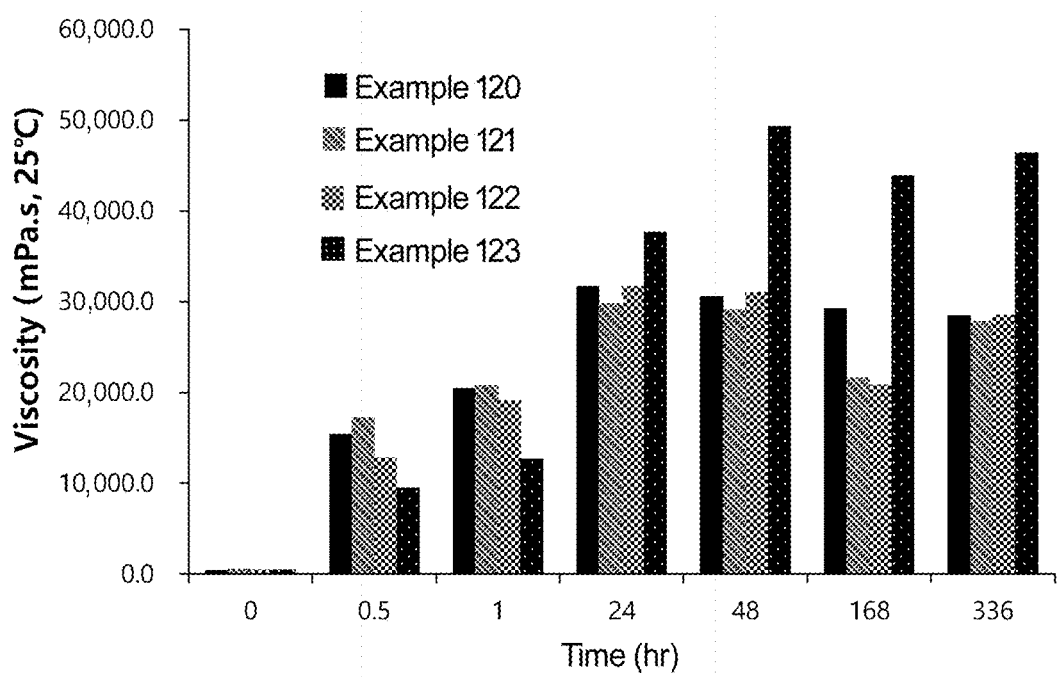
FIG. 4 shows the results obtained by measuring the viscosities, in order to confirm the time capable of forming a robust matrix even despite external forces, when the sustained-release pharmaceutical compositions prepared in Examples 120 to 123 were exposed to an aqueous phase.

Experimental Example 4. Evaluation of Robust Matrix-Forming Ability of Sustained-Release Injectable Pharmaceutical Compositions in the Form of a Lipid Solution The sustained-release injectable pharmaceutical compositions in the form of a lipid solution prepared in Examples 120 to 123 were filled in a 1 ml syringe, and then 100 mg thereof was respectively injected into a glass vial containing 10 ml of pH 7.4 phosphate buffer through a 26 gauge needle, so as to form a matrix. Each glass vial was stored in an oven maintained at 37° C. The matrix in the vial was carefully taken out at each measuring time, the moisture on the surface was eliminated, and then the viscosity of the matrix was measured using a cone-plate rotating viscometer (RM-100 touch, Ramy). The results thereof are shown in FIG. 4. From the results of FIG. 4, the viscosity of the matrix increased rapidly within 30 minutes (0.5 hours), which indicates that the pharmaceutical compositions obtained according to the present invention form a robust matrix capable of maintaining its shape even despite external forces within 30 minutes, when they are exposed to an aqueous phase. Therefore, when the sustained-release injectable pharmaceutical compositions in the form of a lipid solution obtained according to the present invention is injected into a living body, a matrix is also rapidly formed, thereby effectively avoiding the initial burst release of a pharmacologically active substance.

Experimental Example 5. In Vitro Release Tests of Leuprolide Acetate

Figure 5:
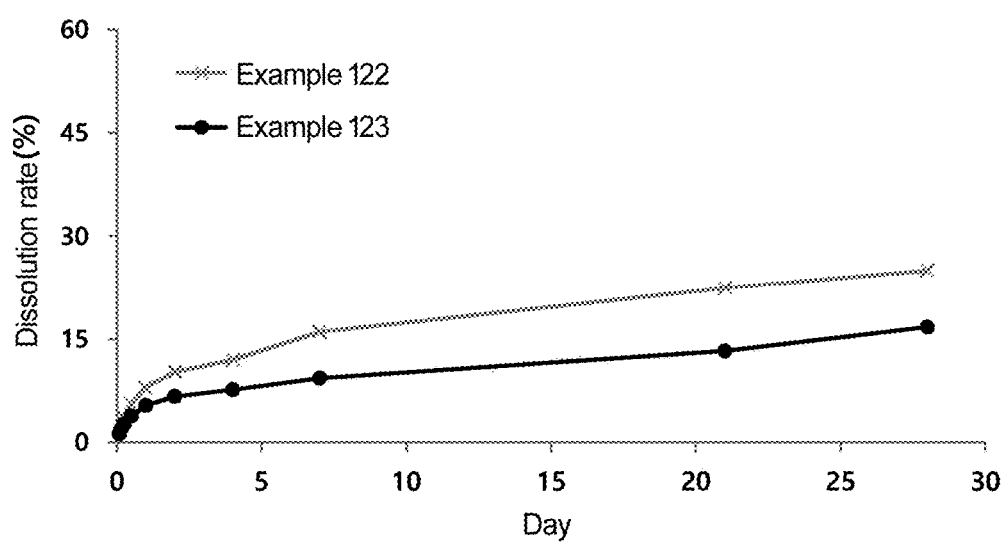
FIG. 5 shows the results of the in vitro release tests for the sustained-release pharmaceutical compositions containing leuprolide acetate prepared in Examples 122 and 123.

Sustained-release effects were confirmed by performing in vitro release tests on the sustained-release injectable pharmaceutical compositions in the form of a lipid solution prepared in Examples 122 and 123. Specifically, a sample container capable of loading the pharmaceutical composition was prepared by attaching 16 mesh and 100 mesh sieves to both sides of an acrylic tube (inner diameter: 14 mm, height: 15 mm). And, a pH 7.0 test solution containing 200 mg of polysorbate 80, 21 ml of triethylamine, and 11 ml of phosphoric acid was prepared. The sample container loaded with 100 mg of each sustained-release injectable pharmaceutical composition in the form of a lipid solution and the test solution were placed in a 40 ml test container (outer diameter: 25 mm, height: 100 mm), which was mounted on a water bath-bottle rotating apparatus (BDSHWB-980R, Bandi Tech). While the apparatus was stirred at 37.5° C. at 25 rpm, the samples were taken for 28 days and then analyzed by HPLC under the following conditions.
<HPLC Conditions>
  Column: 100×4.6 mm, 3 µm packing L1 column
  Mobile phase: pH 3.0 triethylamine solution containing 5% (w/v) of Triton X-100:acetonitrile:n-propyl alcohol=80:12:8 (v/v/v)
  Flow rate: 1.0 ml/min
  Temperature: 20° C.
  Injection volume: 20 µl
  Wavelength: 220 nm (ultraviolet spectrophotometer)
The results obtained by performing the in vitro release tests as described above are shown in FIG. 5. From the results of FIG. 5, it can be confirmed that the sustained-release injectable pharmaceutical compositions in the form of a lipid solution obtained according to the present invention exhibit an effective sustained-release pattern for a long period of time.

Experimental Example 6. In Vitro Release Tests of Goserelin Acetate

Figure 6:
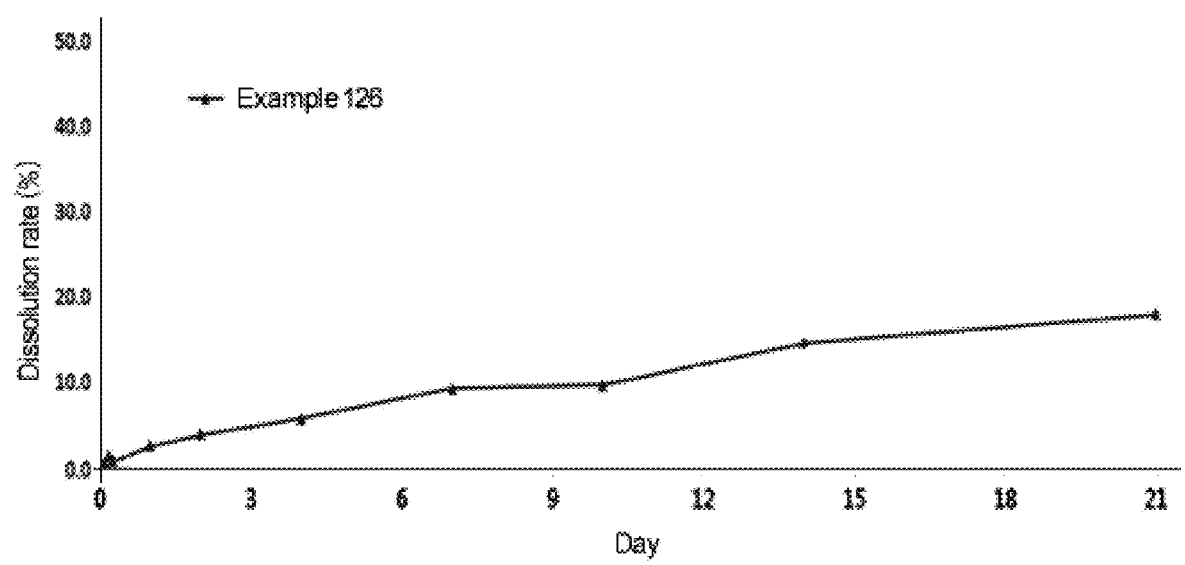
FIG. 6 shows the result of the in vitro release test for the sustained-release pharmaceutical composition containing goserelin acetate prepared in Example 126.

Sustained-release effect was confirmed by performing in vitro release test on the sustained-release injectable pharmaceutical composition in the form of a lipid solution prepared in Example 126. Specifically, a sample container capable of loading the sustained-release lipid solution was prepared by attaching 16 mesh and 100 mesh sieves to both sides of an acrylic tube (inner diameter: 14 mm, height: 15 mm). And, a pH 7.4 phosphate buffer containing 200 mg of polysorbate 80 was prepared as a test solution. The sample container loaded with 200 mg of the sustained-release injectable pharmaceutical composition in the form of a lipid solution and the test solution were placed in a 40 ml test container (outer diameter: 25 mm, height: 100 mm), which was mounted on a water bath-bottle rotating apparatus (BDSHWB-980R, Bandi Tech). While the apparatus was stirred at 37.5° C. at 25 rpm, the samples were taken for 21 days and then analyzed by HPLC under the following conditions.
<HPLC Conditions>
  Column: 150×4.6 mm, 5 µm packing L1 column
  Mobile phase: 0.1% trifluoroacetic acid aqueous solution containing 5% (w/v) of Triton X-100:acetonitrile=75:25 (v/v)
  Flow rate: 1.4 ml/min
  Temperature: 40° C.
  Injection volume: 100 µl
  Wavelength: 220 nm (ultraviolet spectrophotometer)
The result obtained by performing the in vitro release test as described above is shown in FIG. 6. From the result of FIG. 6, it can be confirmed that the sustained-release injectable pharmaceutical composition in the form of a lipid solution obtained according to the present invention exhibits an effective sustained-release to pattern for a long period of time.

The invention claimed is:

1. A sustained-release lipid pre-concentrate for preparing a sustained-release injectable pharmaceutical composition in the form of a lipid solution, consisting of:
    an unsaturated fatty acid having 14 to 20 carbon atoms ($C_{14}$~$C_{20}$);
    a phospholipid;
    α-tocopherol acetate, and
    optionally a biocompatible solvent and/or a medium chain triglyceride,
    wherein the sustained-release lipid pre-concentrate is free of diacyl glycerol and sorbitan unsaturated fatty acid ester; and forms a liquid crystal in an aqueous medium.

2. The pre-concentrate according to claim 1, wherein the unsaturated fatty acid having 14 to 20 carbon atoms ($C_{14}$~$C_{20}$) is present in an amount ranging from 30 to 70 wt % based on the total weight of the preconcentrate.

3. The pre-concentrate according to claim 1, wherein the phospholipid is present in an amount ranging from 25 to 50 wt % based on the total weight of the preconcentrate.

4. The pre-concentrate according to claim 1, wherein the α-tocopherol acetate is present in an amount ranging from 5 to 20 wt % based on the total weight of the preconcentrate.

5. The pre-concentrate according to claim 1, consisting of an unsaturated fatty acid having 14 to 20 carbon atoms ($C_{14}$~$C_{20}$); a phospholipid; α-tocopherol acetate; and a biocompatible solvent,
    wherein the biocompatible solvent is one or more organic solvents selected from the group consisting of ethanol, propylene glycol, N-methylpyrrolidone, and benzyl alcohol; or an aqueous solution of the organic solvent.

6. The pre-concentrate according to claim 5, wherein the biocompatible solvent is present in an amount ranging from 5 to 10 wt % based on the total weight of the preconcentrate.

7. The pre-concentrate according to claim 5, consisting of 30 to 65 wt % of the unsaturated fatty acid having 14 to 20 carbon atoms ($C_{14}$~$C_{20}$); 25 to 50 wt % of the phospholipid;

5 to 20 wt % of α-tocopherol acetate; and 5 to 10 wt % of the biocompatible solvent, based on the total weight of the preconcentrate.

8. The pre-concentrate according to claim 1, consisting of an unsaturated fatty acid having 14 to 20 carbon atoms ($C_{14}$~$C_{20}$); a phospholipid; α-tocopherol acetate; and a medium chain triglyceride.

9. The pre-concentrate according to claim 8, wherein the medium chain triglyceride is present in an amount ranging from 1 to 5 wt % based on the total weight of the preconcentrate.

10. The pre-concentrate according to claim 8, consisting of 30 to 65 wt % of the unsaturated fatty acid having 14 to 20 carbon atoms ($C_{14}$~$C_{20}$); 25 to 50 wt % of the phospholipid; 5 to 20 wt % of α-tocopherol acetate; and 1 to 5 wt % of the medium chain triglyceride, based on the total weight of the preconcentrate.

11. The pre-concentrate according to claim 1, consisting of an unsaturated fatty acid having 14 to 20 carbon atoms ($C_{14}$~$C_{20}$); a phospholipid; α-tocopherol acetate; a biocompatible solvent; and a medium chain triglyceride, wherein the biocompatible solvent is one or more organic solvents selected from the group consisting of ethanol, propylene glycol, N-methylpyrrolidone, and benzyl alcohol; or an aqueous solution of the organic solvent.

12. The pre-concentrate according to claim 11, wherein the medium chain triglyceride is present in an amount ranging from 1 to 5 wt % based on the total weight of the preconcentrate.

13. The pre-concentrate according to claim 11, consisting of 30 to 55 wt % of the unsaturated fatty acid having 14 to 20 carbon atoms ($C_{14}$~$C_{20}$); 25 to 45 wt % of the phospholipid; 5 to 20 wt % of α-tocopherol acetate; 1 to 5 wt % of the medium chain triglyceride; and 5 to 10 wt % of the biocompatible solvent, based on the total weight of the preconcentrate.

14. A sustained-release injectable pharmaceutical composition in the form of a lipid solution, consisting of a pharmacologically active substance; and the pre-concentrate according to claim 1, wherein the sustained-release injectable pharmaceutical composition is free of diacyl glycerol and sorbitan unsaturated fatty acid ester.

15. The pharmaceutical composition according to claim 14, wherein the pharmacologically active substance has a solubility of 0.1 mg/ml or more in the pre-concentrate.

16. The pharmaceutical composition according to claim 15, wherein the pharmacologically active substance is leuprolide or a pharmaceutically acceptable salt thereof; goserelin or a pharmaceutically acceptable salt thereof; entecavir or a pharmaceutically acceptable salt thereof; octreotide or a pharmaceutically acceptable salt thereof; lanreotide or a pharmaceutically acceptable salt thereof; pasireotide or a pharmaceutically acceptable salt thereof; exenatide or a pharmaceutically acceptable salt thereof; liraglutide or a pharmaceutically acceptable salt thereof; albiglutide or a pharmaceutically acceptable salt thereof; lixisenatide or a pharmaceutically acceptable salt thereof; semaglutide or a pharmaceutically acceptable salt thereof; dutasteride or a pharmaceutically acceptable salt thereof; donepezil or a pharmaceutically acceptable salt thereof; aripiprazole or a pharmaceutically acceptable salt thereof; paliperidone or a pharmaceutically acceptable salt thereof; or risperidone or a pharmaceutically acceptable salt thereof.

17. The pharmaceutical composition according to claim 14, consisting of 0.1 to 10 wt % of the pharmacologically active substance; 30 to 60 wt % of the unsaturated fatty acid having 14 to 20 carbon atoms ($C_{14}$~$C_{20}$); 25 to 50 wt % of the phospholipid; and 5 to 20 wt % of α-tocopherol acetate, based on the total weight of the pharmaceutical composition.

18. The pharmaceutical composition according to claim 14, consisting of 0.1 to 10 wt % of the pharmacologically active substance; 30 to 60 wt % of the unsaturated fatty acid having 14 to 20 carbon atoms ($C_{14}$~$C_{20}$); 25 to 45 wt % of the phospholipid; 5 to 20 wt % of α-tocopherol acetate; and 5 to 10 wt % of the biocompatible solvent, based on the total weight of the pharmaceutical composition.

19. The pharmaceutical composition according to claim 14, consisting of 0.1 to 10 wt % of the pharmacologically active substance; 30 to 55 wt % of the unsaturated fatty acid having 14 to 20 carbon atoms ($C_{14}$~$C_{20}$); 25 to 45 wt % of the phospholipid; 5 to 20 wt % of α-tocopherol acetate; 1 to 5 wt % of the medium chain triglyceride; and 5 to 10 wt % of the biocompatible solvent, based on the total weight of the pharmaceutical composition.

* * * * *